(12) United States Patent
Okayama et al.

(10) Patent No.: US 11,122,963 B2
(45) Date of Patent: Sep. 21, 2021

(54) PLUG FOR ENDOSCOPE

(71) Applicants: OSAKA UNIVERSITY, Osaka (JP); PANASONIC I-PRO SENSING SOLUTIONS CO., LTD., Fukuoka (JP)

(72) Inventors: Keita Okayama, Osaka (JP); Shinsuke Nanto, Osaka (JP); Seiji Higashiyama, Fukuoka (JP); Makoto Kamioka, Fukuoka (JP)

(73) Assignees: OSAKA UNIVERSITY, Osaka (JP); PANASONIC I-PRO SENSING SOLUTIONS CO., LTD., Fukuoka (JP)

( * ) Notice: Subject to any disclaimer, the term of this patent is extended or adjusted under 35 U.S.C. 154(b) by 313 days.

(21) Appl. No.: 16/131,803

(22) Filed: Sep. 14, 2018

(65) Prior Publication Data
US 2019/0082938 A1 Mar. 21, 2019

(30) Foreign Application Priority Data
Sep. 15, 2017 (JP) .............................. JP2017-177949

(51) Int. Cl.
*A61B 1/00* (2006.01)
*A61B 1/04* (2006.01)
*A61B 1/07* (2006.01)

(52) U.S. Cl.
CPC ...... *A61B 1/00124* (2013.01); *A61B 1/00126* (2013.01); *A61B 1/00135* (2013.01);
(Continued)

(58) Field of Classification Search
CPC ............ A61B 1/00124; A61B 1/00126; A61B 1/00135; A61B 1/00137; A61B 1/04; A61B 1/07; A61B 1/00128; A61M 2005/506
(Continued)

(56) References Cited

U.S. PATENT DOCUMENTS 5,469,841 A * 11/1995 Kobayashi ......... A61B 1/00124
600/158
5,810,620 A 9/1998 Kobayashi et al.
(Continued)

FOREIGN PATENT DOCUMENTS

EP 2656779 A1 * 10/2013 ......... A61B 1/00119
JP 61-248017 11/1986
(Continued)

*Primary Examiner* — Matthew J Kasztejna
*Assistant Examiner* — Christen Hicks
(74) *Attorney, Agent, or Firm* — Greenblum & Bernstein, P.L.C.

(57) ABSTRACT

Plug for endoscope includes a flexible tube-shaped sheath through which a plurality of wires are inserted. The plurality of wires is connected to an insertion tip portion having an image capturing portion. The plug includes a housing having a substrate accommodation portion and a sheath introduced portion. The substrate accommodation portion accommodates a substrate, a base end aperture portion of the sheath passed through an opening of the housing is arranged in the sheath introduced portion, and a part of the plurality of wires derived from the base end aperture portion is connected to the substrate. A liquid intrusion prevention wall is provided to stand on a bottom wall of the housing, and the bottom wall is arranged under the base end aperture portion of the sheath in a substantially vertical direction, and the substrate accommodation portion and the sheath introduced portion are spatially isolated from each other.

20 Claims, 15 Drawing Sheets

(52) U.S. Cl.
CPC ............ *A61B 1/00137* (2013.01); *A61B 1/04* (2013.01); *A61B 1/07* (2013.01)

(58) Field of Classification Search
USPC ......................... 600/132, 134, 186, 133, 136
See application file for complete search history.

(56) References Cited

U.S. PATENT DOCUMENTS

| | | |
|---|---|---|
| 2003/0216613 A1 | 11/2003 | Suzuki et al. |
| 2009/0216081 A1 | 8/2009 | Suzuki et al. |
| 2013/0090526 A1 | 4/2013 | Suzuki et al. |

FOREIGN PATENT DOCUMENTS

| | | | | |
|---|---|---|---|---|
| JP | 06-250103 | | 9/1994 | |
| JP | 06-251829 | | 9/1994 | |
| JP | 2000340290 A | * | 12/2000 | |
| JP | 2001161642 A | * | 6/2001 | |
| JP | 2003-190085 | | 7/2003 | |
| JP | 2003-284722 | | 10/2003 | |
| JP | 2003-325529 | | 11/2003 | |
| JP | 5389731 B2 | * | 1/2014 | |
| JP | 2014188206 A | * | 10/2014 | ............... A61B 1/07 |
| JP | 2015-002864 | | 1/2015 | |
| WO | 2014/156168 | | 10/2014 | |

* cited by examiner

PLUG FOR ENDOSCOPE

BACKGROUND OF THE INVENTION

1. Field of the Invention

The present disclosure relates to a plug for endoscope.

2. Description of the Related Art

For example, there is a possibility that an endoscope inserted into the body of a patient may cause the inside and the outside of the body to communicate with each other due to a flexible tube. For example, in an endoscope system of Patent Document 1, sealing means is provided on a hand side of a suture unit and an endoscope. This sealing means includes an inner tube having an inner diameter allowing the endoscope to pass through, and an outer tube having an inner diameter greater than that of the inner tube and causing the inner tube to be inserted through the outer tube. An outer diameter of the outer tube is slightly greater than an inner diameter of a hole of a valve. A plurality of tubes and the like pass through a space formed between the inner tube and the outer tube. A sealing member fills the space between the tubes. Spaces between both ends of the inner tube and the endoscope are sealed by a tape. Accordingly, an over-tube can be reliably sealed with respect to the suture unit and the endoscope, and air leakage is prevented when air is fed into a body cavity and the body cavity is inflated.

However, on the assumption of an endoscope which is inserted into a duct having a small diameter, such as a blood vessel of a human body, and observes the inside thereof, it is difficult to seal a space between a flexible tube-shaped sheath and a plurality of wires internally inserted through the sheath, by using a valve having a configuration of a technology in the related art as that in JP-A-2003-284722.

Since an endoscope inserted into a blood vessel of a patient has a small diameter (for example, the maximum outer diameter of approximately 2 mm or smaller), there is a possibility that a sheath may be damaged due to contact or the like with a foreign substance. Therefore, it is not possible to completely deny a possibility that body fluid such as blood, or a contrast medium, a physiological saline solution, or other liquid medicines (which will hereinafter be referred to as "liquid") used at the time of an examination or a surgical operation may intrude into the sheath when the sheath is inserted into a blood vessel. In regard to liquid that has intruded into the sheath, if the amount of intrusion is significant, the liquid flows into an instrument (for example, a housing of a plug for endoscope) on the hand side from a base end aperture portion of the sheath along a wire rod due to a capillary phenomenon. If liquid that has flowed in adheres to an electrical component, such as a substrate, inside the housing and causes a short circuit, there is a possibility that a patient may be affected by an electric shock. In addition, as in the configuration of the technology in the related art, it is possible to conceive that a space formed between a sheath and a wire rod is sealed against liquid flowing along the inside of the sheath, by filling the space with a sealing member. Incidentally, in an endoscope inserted into a blood vessel, a light fiber has particularly low strength due to the small diameter. In a bundle of wires, if both ends thereof in an extending direction are integrally fixed, in a case of being bent, the wires tend to swell inside a sheath due to the difference in the radius of curvature. In this case, if the swelling is restricted by an inner circumferential wall of the sheath, a possibility of damage to a light fiber having a particularly small diameter increases.

SUMMARY OF THE INVENTION

The present disclosure has been devised in consideration of the foregoing circumstances in the related art, and an object thereof is to provide a plug for endoscope, in which an electric shock to a patient can be minimized when liquid intrudes into a sheath.

According to the present disclosure, there is provided a plug for endoscope including a flexible tube-shaped sheath through which a plurality of wires are inserted. The plurality of wires is connected to an insertion tip portion having an image capturing portion. The plug for endoscope includes a housing having a substrate accommodation portion and a sheath introduced portion. The substrate accommodation portion accommodates a substrate, a base end aperture portion of the sheath passed through an opening of the housing is arranged in the sheath introduced portion, and a part of the plurality of wires derived from the base end aperture portion is connected to the substrate. A liquid intrusion prevention wall is provided to stand on a bottom wall of the housing, and the bottom wall is arranged under side of the base end aperture portion of the sheath in a substantially vertical direction, and the substrate accommodation portion and the sheath introduced portion are spatially isolated from each other.

In addition, according to the present disclosure, there is provided a plug for endoscope including a flexible tube-shaped sheath through which a plurality of wires are inserted. The plurality of wires is connected to an insertion tip portion having an image capturing portion. The plug for endoscope includes a housing having a substrate accommodation portion and a sheath introduced portion. The substrate accommodation portion accommodates a substrate, and a base end aperture portion of the sheath passed through an opening of the housing is arranged in the sheath introduced portion. A part of the plurality of wires derived from the base end aperture portion is connected to the substrate. The substrate accommodation portion of the housing is covered with a water-tight structure so that the substrate accommodation portion and a sheath introduced portion are spatially isolated from each other, the sheath being arranged in the sheath introduced portion.

In addition, according to the present disclosure, there is provided a plug for endoscope including a flexible tube-shaped sheath through which a plurality of wires are inserted. The plurality of wires is connected to an insertion tip portion having an image capturing portion. The plug for endoscope includes a housing having a substrate accommodation portion and a sheath introduced portion. The substrate accommodation portion accommodates a substrate, a base end aperture portion of the sheath passed through an opening of the housing is arranged in the sheath introduced portion, and a part of the plurality of wires derived from the base end aperture portion is connected to the substrate. The plug for endoscope includes a cover that is provided inside the housing, is water-tightly penetrated by a part of the plurality of wires, and water-tightly covers the substrate.

According to the present disclosure, an electric shock to a patient can be minimized when liquid intrudes into a sheath.

DETAILED DESCRIPTION OF THE PREFERRED EMBODIMENTS

Hereinafter, with reference to the appropriate drawings, embodiments in which plugs for endoscope according to the present disclosure are specifically disclosed will be described in detail. However, more detailed description than is necessary may be omitted. For example, detailed description for well-known matters or duplicated description for the substantially same configuration is omitted sometimes, in order to avoid the following description being unnecessarily redundant and to make the following description easy for those skilled in the art to understand. The accompanying drawings and the following description are provided to make those skilled in the art sufficiently understand the present disclosure, and these are not intended to limit the gist disclosed in the aspects of the present disclosure.

Embodiment 1

Figure 1:
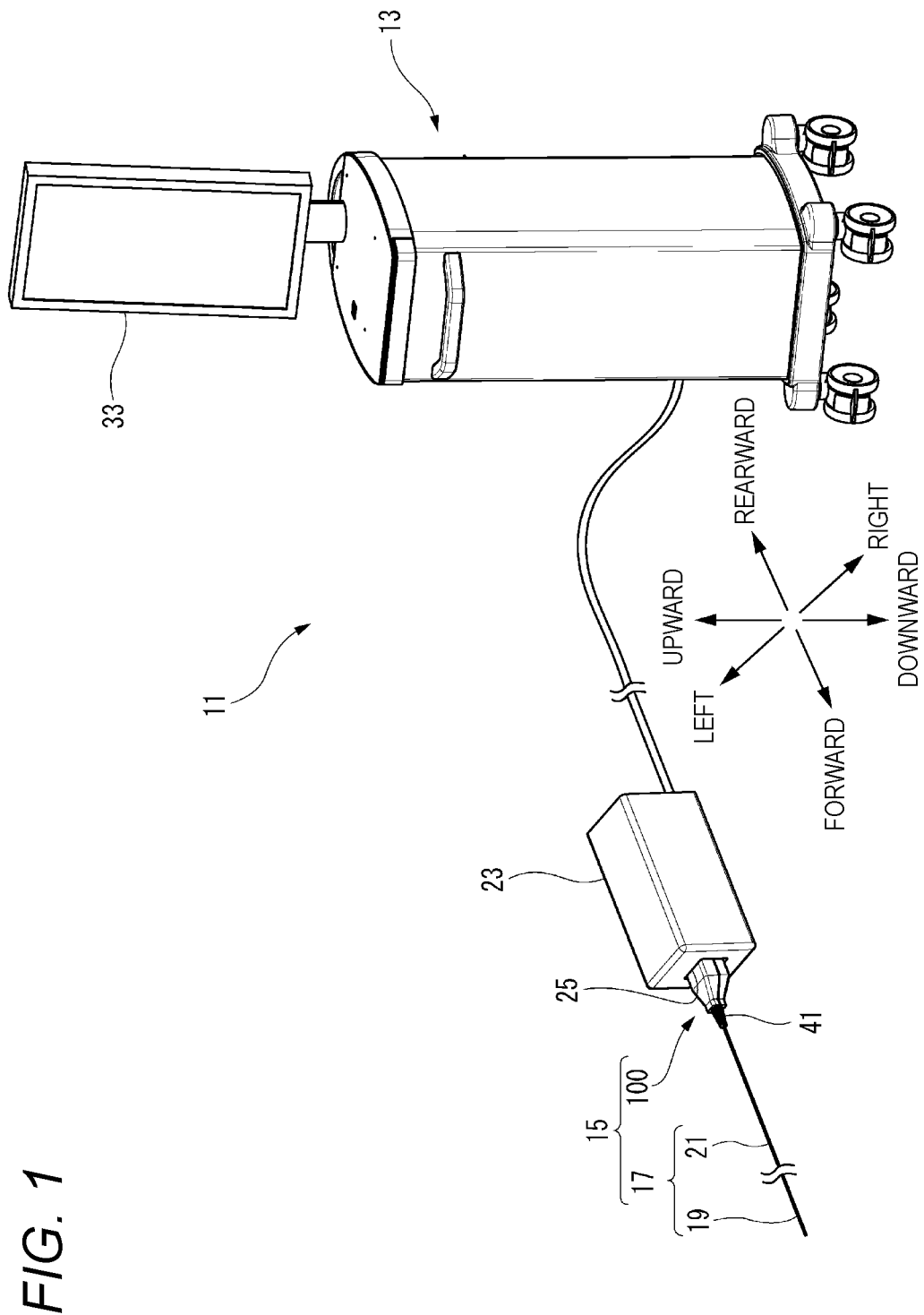
FIG. 1 is a view of an overall configuration illustrating an example of an endoscope system including a plug for endoscope of Embodiment 1.

FIG. 1 is a view of an overall configuration illustrating an example of an endoscope system 11 including a plug 100 for endoscope of Embodiment 1.

Directions used in description of this specification comply with the directions of arrows illustrated in FIG. 1. Here, for example, "upward" and "downward" respectively correspond to an upward direction on a display apparatus (for example, a monitor device 33, which will be described below) side of a console 13 placed on a horizontal surface (for example, a floor surface) of an operating room or the like, and a downward direction on a console main body side, and "forward (tip)" and "rearward" respectively correspond to an inserted tip portion 19 side of an endoscope 15 and a base end side of the plug 100 for endoscope (in other words, the console 13 side).

For example, the endoscope system 11 is configured to include the endoscope 15 that is a soft scope for medical use, and the console 13 which performs known image processing and the like with respect to a still image or a motion image obtained by the endoscope 15 capturing an image of the inside of an observation target (for example, a blood vessel of a human body). The endoscope 15 is configured to include an inserted portion 17 and the plug 100 for endoscope. The inserted portion 17 is configured to include the inserted tip portion 19 and a soft portion 21 connected to the inserted tip portion 19. The endoscope 15 includes an image capturing portion (not illustrated) constituted of a lens and an image capturing element in the inserted tip portion 19. In other words, in the example of the configuration of the endoscope 15 of Embodiment 1, the image capturing portion includes an image capturing element (not illustrated). The endoscope 15 is also referred to as a catheter. In the endoscope 15, the image capturing portion of the inserted tip portion 19 includes the image capturing element. However, the plug 100 for endoscope of Embodiment 1 may be applied to a fiber endoscope having no image capturing element in the image capturing portion on the inserted tip portion 19 side.

A cable is connected to the console 13, and a relay unit 23 is attached to a tip of the cable. The relay unit 23 has a socket portion 25. A rear portion of the plug 100 for endoscope of the endoscope 15 is inserted into the socket portion 25. Accordingly, the endoscope 15 can transmit and receive electricity and various signals (a video image signal, a control signal, and the like) with respect to the console 13 and can transmit illumination light.

The soft portion 21 has an appropriate length suitable for a method such as various kinds of endoscopic examinations and endoscopic operations. For example, the soft portion 21 has a configuration in which the outer circumference of a spirally wound thin metal plate is covered with a net, and the outer circumference is covered with a sheath 27 (refer to FIG. 4) that is a covering. The soft portion 21 is formed to have sufficient flexibility at the time of an endoscopic examination or at the time of an endoscopic operation, for example. The soft portion 21 connects the inserted tip portion 19 and the plug 100 for endoscope to each other.

The electricity and various signals described above are guided from the inserted tip portion 19 to the plug 100 for endoscope through a transmission cable 29 that is a wire rod inserted through the inside of the soft portion 21, and light fibers 31 (refer to FIG. 4) that are an example of glass fibers. Image data output by the image capturing element provided in the inserted tip portion 19 is relayed by the relay unit 23 from the plug 100 for endoscope through the transmission cable 29 and is transmitted to the console 13 including a computer. The console 13 performs known image processing such as correction and tone correction using the computer with respect to image data transmitted from the image capturing element and outputs image-processed image data to the display apparatus. For example, the display apparatus is the monitor device 33 having a display device such as a liquid crystal display panel and displays an image (for example, image data indicating a condition inside a blood vessel of a human body that is an image target) of an image target captured by the endoscope 15.

The endoscope 15 can be inserted into a body cavity having a small diameter due to the inserted portion 17 having a small diameter. The body cavity having a small diameter is not limited to a blood vessel of a human body. Examples thereof include the urinary duct, the pancreatic duct, the bile duct, and a bronchiole. That is, the endoscope 15 can be inserted into a blood vessel, the urinary duct, the pancreatic duct, the bile duct, a bronchiole, and the like of a human body. The endoscope 15 can be used for an observation of a lesion inside a blood vessel. For example, the endoscope 15 is effective in identifying atherosclerotic plaque. In addition, the endoscope 15 can also be applied to an observation at the time of a cardiac catheter examination. Moreover, the endoscope 15 is also effective in detecting a thrombus or arteriosclerotic yellow plaque. In an atherosclerotic lesion, the tone (white, light yellow, or yellow) and the surface (smooth or uneven) are observed. In a thrombus, the tone (red, white, dark red, yellow, brown, or mixed color) is observed.

In addition, the endoscope 15 can be used for diagnosis and treatment of renal pelvis cancer, urinary duct cancer, and idiopathic renal bleeding. In this case, the endoscope 15 is inserted into the bladder through the urethra and advances to the inside of the urinary duct, so that the insides of the urinary duct and the renal pelvis can be observed.

In addition, the endoscope 15 can be inserted into a papilla of Vater open in the duodenum. Bile is secreted by the liver and passes through the bile duct, and pancreatic juice is secreted by the pancreas and passes through the pancreatic duct. Then, they are drained from papillae of Vater in the duodenum. It is possible to observe the bile duct or the pancreatic duct by using the endoscope 15 being inserted through a papilla of Vater that is an aperture portion of the bile duct or the pancreatic duct.

Moreover, the endoscope 15 can be inserted into the bronchus. The endoscope 15 is inserted through the oral cavity or the nasal cavity of an examinee (that is, an operation patient) in a supine position. The endoscope 15 passes through the pharynx and the larynx and is inserted into the trachea while visually checking the vocal cords. The bronchus becomes thinner every time it is branched. For example, a lumen to a subsegmental bronchus can be checked with an endoscope 15 having the maximum outer diameter Dmax smaller than 2 mm.

Hereinafter, an example of a case where the endoscope 15 is used for observing the inside of a blood vessel of a human body will be described.

Figure 2:
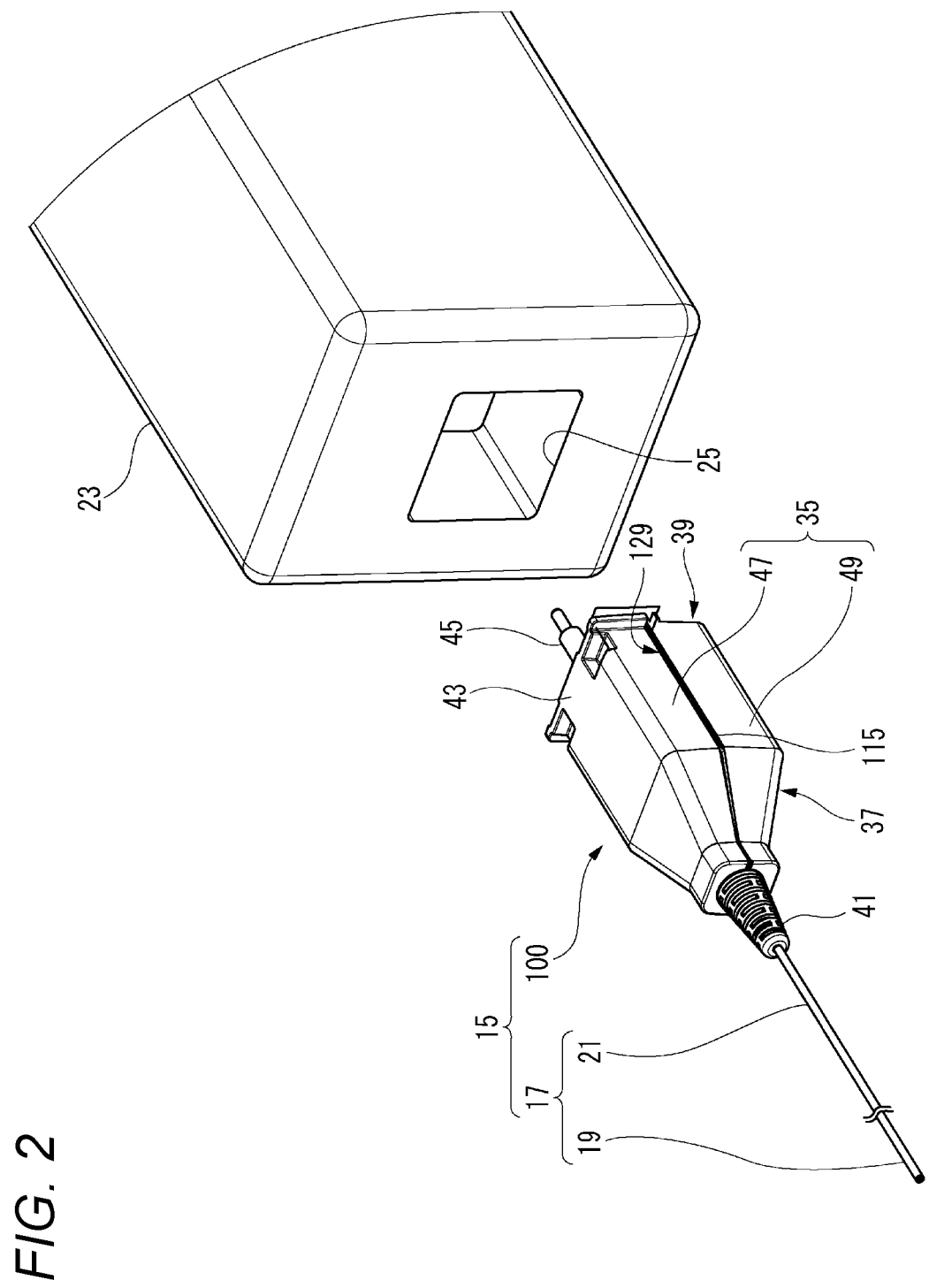
FIG. 2 is an exploded perspective view of an endoscope and a relay unit illustrated in FIG. 1.

FIG. 2 is an exploded perspective view of the endoscope 15 and the relay unit 23 illustrated in FIG. 1.

The plug 100 for endoscope of Embodiment 1 has a housing 35 connected to a rear end of the inserted portion 17. In the housing 35, a substantially quadrangular pyramid-shaped sheath introduced portion 37, into which the sheath 27 is introduced (inserted), is formed on a fixed side. The sheath introduced portion 37 is disposed such that an axis line perpendicular to a substantially quadrangular pyramid-shaped bottom surface and passing through the apex portion lies in a direction along the wire rod.

The housing 35 is formed by connecting a quadrangular cylinder-shaped housing main body 39 to the substantially quadrangular pyramid-shaped bottom surface side having the shape of the sheath introduced portion 37. The sheath 27 is protected by causing a connection part with respect to the sheath introduced portion 37 to penetrate a boot 41 for regulating bending of fiber. The boot 41 is made of a soft material such as rubber, and a plurality of circumferential grooves for applying suitable bendability are formed around the boot 41. A ferrule 45 (which will be described below) protrudes from a rear end portion 43 of the housing 35.

The relay unit 23 is provided with the socket portion 25 into which a joining portion of the housing 35 is fitted. The socket portion 25 includes at least a light emitting element (not illustrated), a card edge connector (not illustrated), and the like. The rear end portion of the housing 35 is joined to the socket portion 25 in a freely attachable/detachable manner. Locking means (not illustrated) is provided across both members, the socket portion 25 and the housing 35. The locking means locks the joining state and unlocks the joining state of the socket portion 25 and the housing 35.

Figure 3:
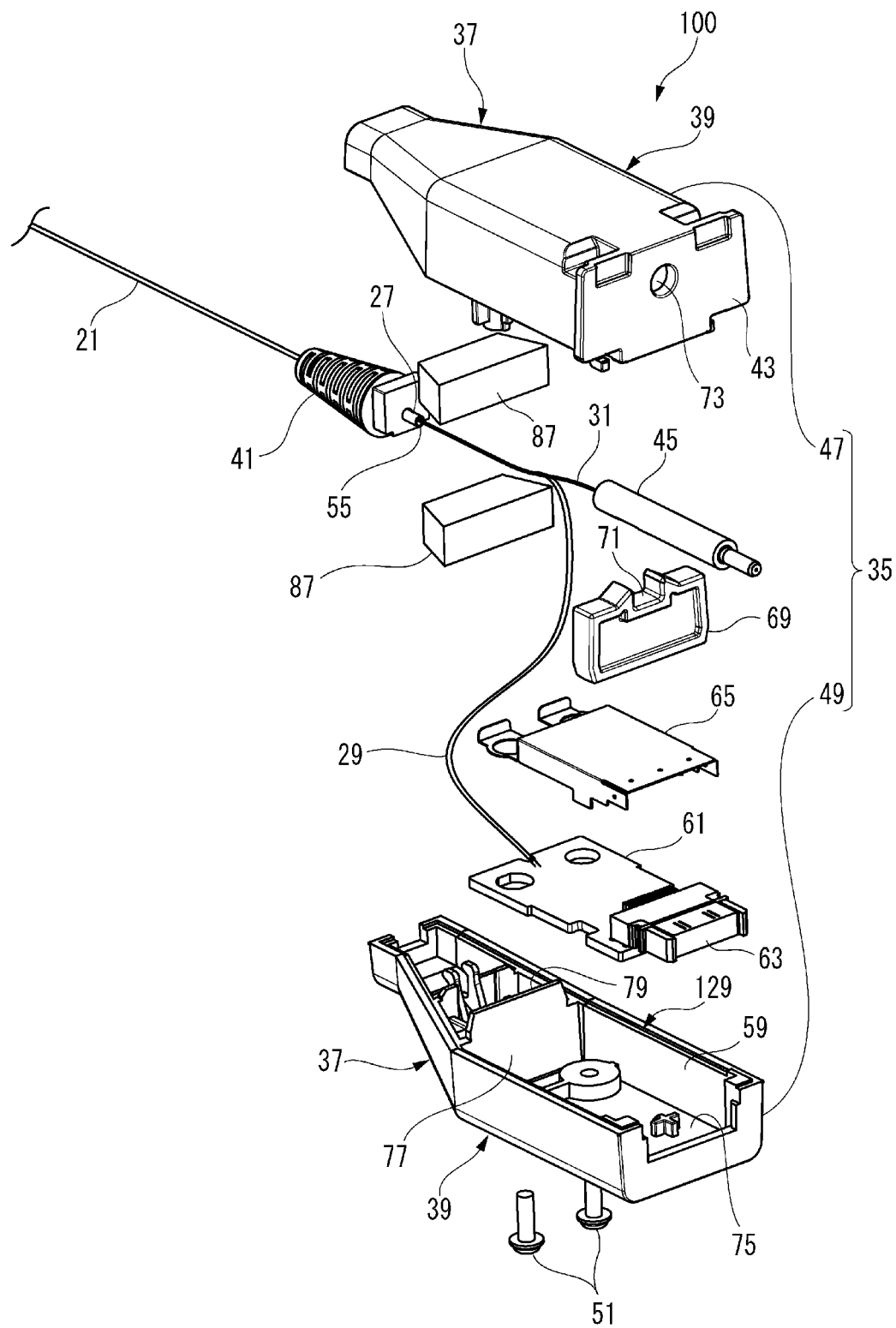
FIG. 3 is an exploded perspective view of the plug for endoscope of the endoscope illustrated in FIG. 2.

FIG. 3 is an exploded perspective view of the plug 100 for endoscope of the endoscope 15 illustrated in FIG. 2.

For example, the housing 35 is configured to be bisected into an upper housing 47 and a lower housing 49 with an axis line of the substantially quadrangular pyramid shape as a boundary. Therefore, in the housing 35, the upper housing 47 and the lower housing 49 are integrally assembled, a front portion of the housing 35 becomes the substantially quadrangular pyramid-shaped sheath introduced portion 37, and the rear portion of the housing 35 can be considered as the quadrangular cylinder-shaped housing main body 39. That is, each of the upper housing 47 and the lower housing 49 is formed in a boat shape having the sheath introduced portion 37 as the stem side. The upper housing 47 and the lower housing 49 are integrally fixed to each other by screwing a plurality of fixing screws 51 inserted through the lower housing 49 into the upper housing 47.

An engagement groove 53 (refer to FIG. 7) of the boot 41 in a circumferential direction is sandwiched by the upper housing 47 and the lower housing 49, so that its rotation and movement in a direction along the axis line are regulated with respect to the sheath introduced portion 37, thereby being fixed. The sheath 27 protrudes on a rear end surface of the boot 41. That is, a base end aperture portion 55 of the sheath 27 is open inside the housing 35.

Figure 4:
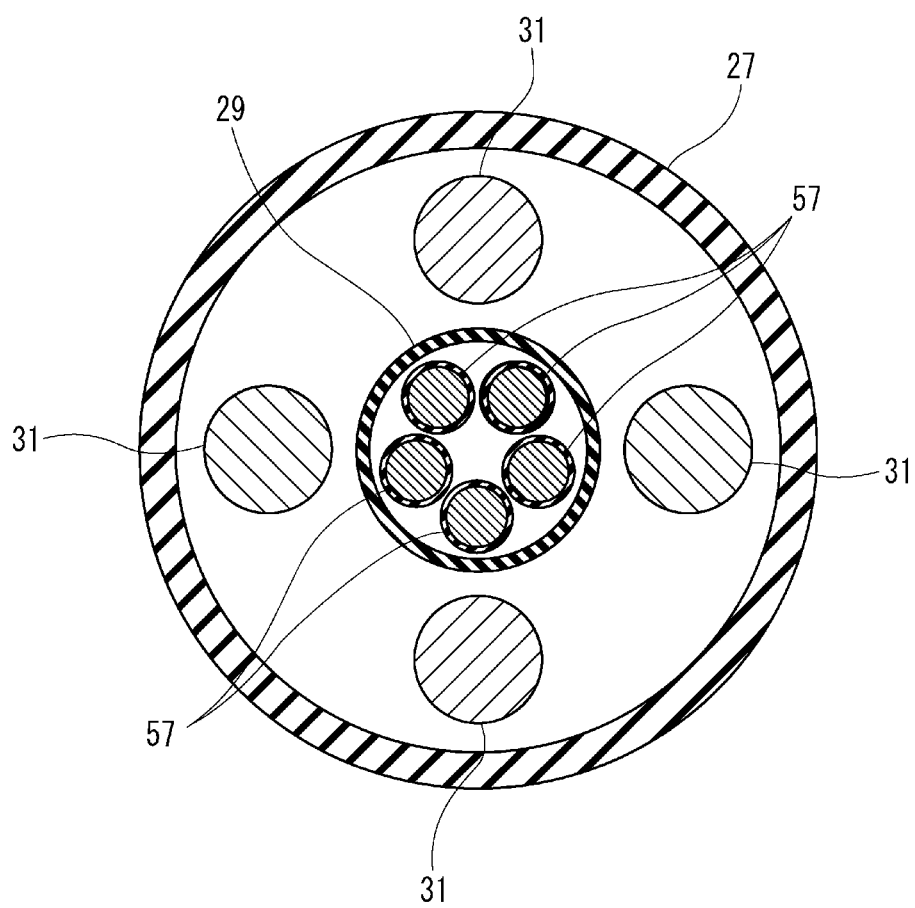
FIG. 4 is a cross-sectional view of a sheath.

FIG. 4 is a cross-sectional view of the sheath 27.

The sheath 27 constitutes a covering of the soft portion 21 described above. The sheath 27 is made of a flexible resin material, and its outer circumference is formed in a circular tube shape. The sheath 27 is connected to the inserted tip portion 19 by causing a tip aperture portion to be fitted into the inserted tip portion 19. The conductive transmission cable 29 and the light fibers 31 that are a plurality of wires connected to the inserted tip portion 19 are internally inserted through the sheath 27. The transmission cable 29 has a plurality of wirings 57 (for example, a signal wire, an electric wire, and a ground wire). In the illustrated example, five wirings 57 are exemplified. However, the number of wirings 57 is not limited thereto. A plurality of light fibers 31 are longitudinally laid along the transmission cable 29. In the illustrated example, four light fibers 31 are exemplified. However, the number of light fibers 31 is not limited thereto. The transmission cable 29 and each of the light fibers 31 are bundled in a non-fixed manner so as to be relatively slidable with each other and are internally inserted through the sheath 27.

In other words, since the conductive transmission cable 29 and the light fibers 31 that are a plurality of wires derived from the base end aperture portion 55 of the sheath 27 are not fixed to the inside of the sheath 27 and the base end aperture portion 55, relative sliding properties of the transmission cable 29 and the light fibers 31 that are a plurality of wires are maintained without being hindered inside the sheath 27, at the base end aperture portion 55, and inside the housing 35 when the sheath 27 is bent. Accordingly, even in a case where the sheath 27 is bent, since there is no damage to the transmission cable 29 and the light fibers 31, transmission efficiency of data does not deteriorate.

In addition, it is desirably that the conductive transmission cable 29 and the light fibers 31 that are a plurality of wires derived from the base end aperture portion 55 of the sheath 27 are disposed with sufficient flexibility inside the sheath 27 and inside the plug for endoscope. As a result, relative sliding properties of the transmission cable 29 and the light fibers 31 that are a plurality of wires are maintained without being hindered inside the sheath 27, at the base end aperture portion 55, and inside the housing 35 when the sheath 27 is bent. Accordingly, even in a case where the sheath 27 is bent, since there is no damage to the transmission cable 29 and the light fibers 31, transmission efficiency of data does not deteriorate.

For example, plastic optical fibers (POF) are preferably used as the light fibers 31. In the plastic optical fibers, a core and a clad are formed of plastic with silicon resin or acrylic resin as a material. In addition, glass fibers in which at least the core of the core and the clad is formed of a glass material such as quartz may be used as the light fibers 31. In this case, the clad may be formed of quartz or may be formed of silicon or a fluorine-based polymer. Accordingly, since the wires are constituted of the light fibers 31 as an example of the transmission cable 29 and glass fibers, rigidity of the wires is ensured, and deterioration in transmission efficiency of data is minimized.

In addition, for example, the light fibers 31 may be a bundle of fibers (bundle fiber) in which a plurality of light fiber element wires are bundled and terminal metal fittings are attached to both ends thereof. Tip surfaces of the light fibers 31 form four emission end surfaces at the inserted tip portion 19, and the base ends are collectively connected to the ferrule 45. For example, a light source is an LED provided in the socket portion 25 or the like. In the endoscope 15, the housing 35 is connected to the socket portion 25, so that light from the LED is emitted from the tip along the light fibers 31. According to this configuration, an image of a dark portion can be captured by using the endoscope 15 alone.

A substrate accommodation portion 59 is provided in the housing main body 39. A substrate 61, to which the transmission cable 29 (wire rod) is connected, is disposed in the substrate accommodation portion 59. A card edge terminal 63 exposed on the rear end surface of the housing main body 39 is provided in the substrate 61. The card edge terminal 63 is connected to the card edge connector of the socket portion 25.

A shield sheet metal 65 is attached to the substrate accommodation portion 59. The shield sheet metal 65 is connected to the ground wire and shields the substrate 61 against electromagnetic noise. The shield sheet metal 65 is formed in a box shape so as to cover the upper surface side of the substrate 61. The substrate 61 is covered with the shield sheet metal 65, so that adhering of liquid 67 (for example, body fluid such as blood of a human body, which will be described below (refer to FIG. 7)) can be minimized.

A ferrule presser 69 is assembled in the rear portion of the housing main body 39. A recessed portion 71 holding the ferrule 45 is formed at an upper edge in the ferrule presser 69. The ferrule 45 inserted into the recessed portion 71 is sandwiched by the ferrule presser 69 and the upper housing 47, and its rotation and movement in an axial direction are regulated, thereby being supported inside the housing. In the supported ferrule 45, the rear end side protrudes from a ferrule derivation hole 73 bored in the rear end portion 43 of the housing 35. For example, light emitted from the LED provided in the socket portion 25 is incident on the ferrule 45.

In this manner, the housing 35 accommodates the substrate 61 and the ferrule 45. In addition, in the housing 35, the base end outer circumferential portion of the sheath 27 is fixed, and the base end aperture portion 55 of the sheath 27 is internally open. In addition, the housing 35 connects the transmission cable 29 that is a part of the wires derived from the base end aperture portion 55 to the substrate 61 and connects the light fibers 31 that is the remaining wires to the ferrule 45.

In the endoscope 15, it is not possible to completely deny a possibility that the sheath 27 having a small diameter (outer diameter of approximately 2 mm or smaller) may be damaged due to contact or the like with a foreign substance and the liquid 67 intrudes into the sheath, when the inserted tip portion 19 and the sheath 27 are inserted into a blood vessel of a patient. For example, in regard to the liquid 67 that has intruded into the sheath, if the amount of intrusion is significant, the liquid 67 flows into the housing from the base end aperture portion 55 of the sheath 27 along the wires due to a capillary phenomenon.

Therefore, as illustrated in FIG. 3, a liquid intrusion prevention wall 77 restraining the liquid 67 from intruding into the substrate accommodation portion 59, in which the substrate 61 is disposed, is formed to stand on a bottom wall 75 of the lower housing 49. The bottom wall 75 is formed as a bottom part including both portions, the sheath introduced portion 37 and the substrate accommodation portion 59 of the lower housing 49. Specifically, the bottom wall 75 tilts in the sheath introduced portion 37 and extends in a horizontal direction in the substrate accommodation portion 59. The liquid intrusion prevention wall 77 is continuously formed from the left to the right in the lower housing 49 at a substantially middle part in a forward/rearward direction of the bottom wall 75. In the lower housing 49, an upper space of the bottom wall 75 is partitioned into the sheath introduced portion 37 and the substrate accommodation portion 59 by the liquid intrusion prevention wall 77. A trapezoidal lower engagement plate portion 79 is formed at the upper edge of the liquid intrusion prevention wall 77.

In this manner, in the plug 100 for endoscope, the liquid intrusion prevention wall 77 restraining the liquid 67 from intruding into the substrate accommodation portion 59, in which the substrate 61 is disposed, is formed to stand on the bottom wall 75 of the housing 35 below the base end aperture portion 55 in a vertical direction so as to have a structure in which the substrate accommodation portion 59 and the sheath introduced portion 37 are spatially isolated from each other. That is, the liquid intrusion prevention wall 77 serves as a partition wall spatially isolating the sheath introduced portion 37 and the substrate accommodation portion 59 from each other.

Figure 5:
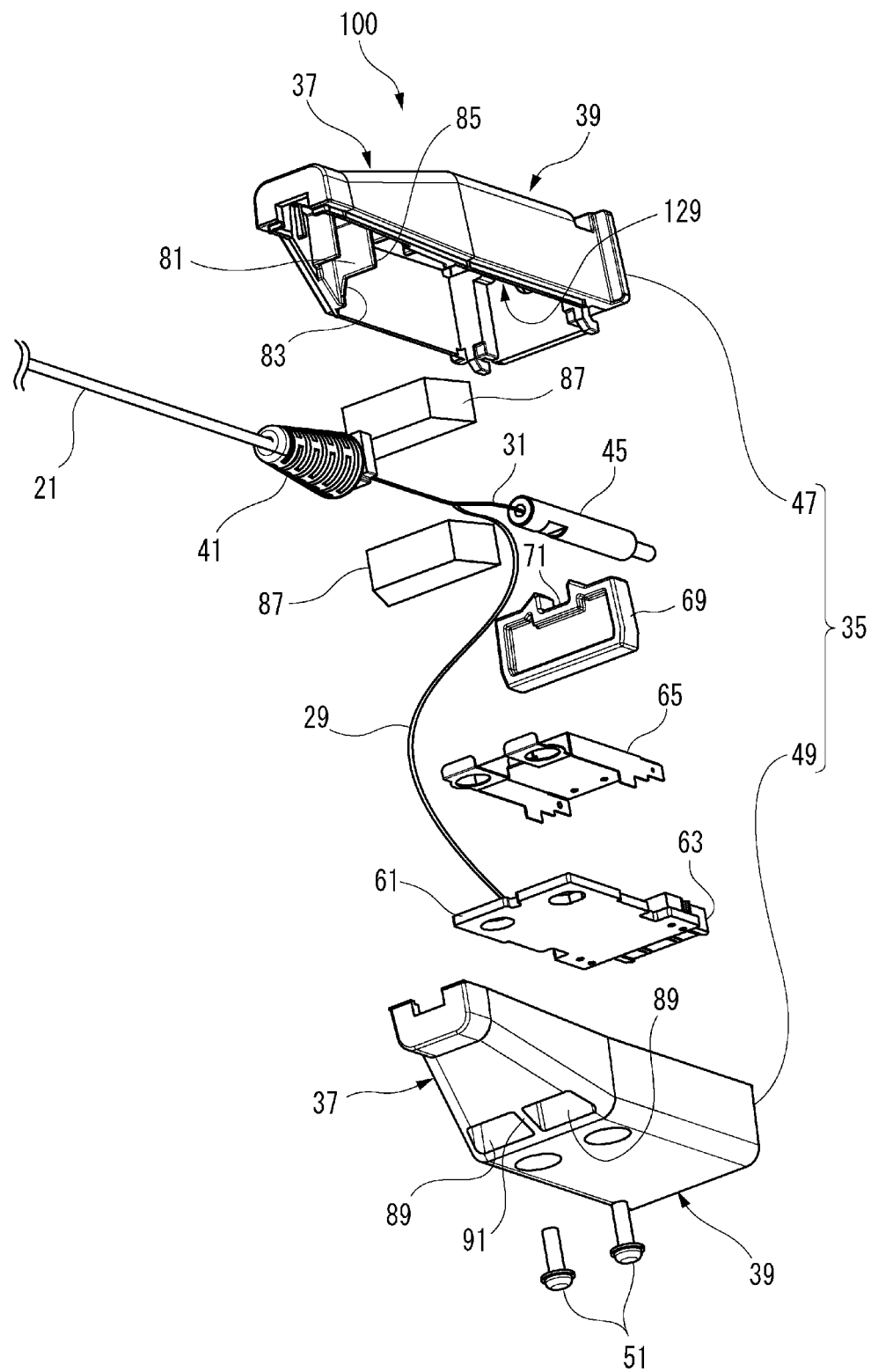
FIG. 5 is an exploded perspective view of the plug for endoscope in FIG. 3 seen from below on a right front side.

FIG. 5 is an exploded perspective view of the plug 100 for endoscope in FIG. 3 seen from below on a right front side.

An upper engagement plate portion 81 engaging with the lower engagement plate portion 79 is hung in the upper housing 47. A trapezoidal cut-out portion 83 with which the trapezoidal lower engagement plate portion 79 engages is formed at a lower edge of the upper engagement plate portion 81. A window portion 85 cut out further upward from the cut-out portion 83 is formed in the upper engagement plate portion 81. The transmission cable 29 and the light fibers 31 pass through the window portion 85. The lower engagement plate portion 79 and the upper engagement plate portion 81 also serve as stoppers regulating rearward movement of sponges 87, which will be described below.

Figure 6:
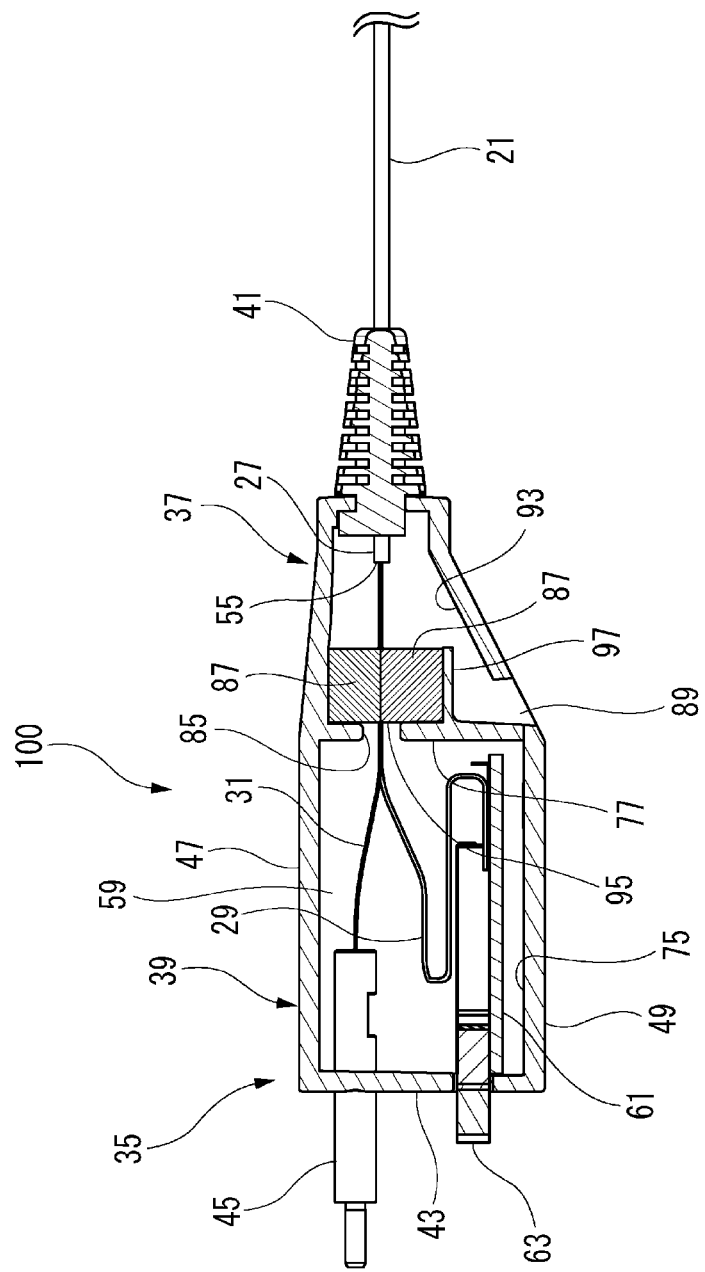
FIG. 6 is a longitudinal cross-sectional view of the plug for endoscope.

FIG. 6 is a longitudinal cross-sectional view of the plug 100 for endoscope.

A drainage hole 89, which is open in the bottom wall 75 below the base end aperture portion 55 of the sheath 27 in the vertical direction and drains body fluid (liquid 67), for example, blood of a human body that has flowed in from the base end aperture portion 55 out of the housing 35 is formed in the sheath introduced portion 37 of the lower housing 49. The drainage hole 89 is not necessarily located immediately below the base end aperture portion 55. In the plug 100 for endoscope of Embodiment 1, the drainage hole 89 is formed in a slender slit shape along the liquid intrusion prevention wall 77.

A rib 91, which extends along the wires immediately below the wires and connects both ends in the extending direction to the inner circumference of the drainage hole, is formed in the drainage hole 89. The rib 91 is disposed at a position bisecting the drainage hole 89 formed in a slit shape, in a longitudinal direction. In other words, the rib 91 connects a pair of facing positions on the inner circumferential side of the drainage hole 89 formed in a slit shape to each other with both ends of the rib 91 in the extending direction.

A tilted plate 93 having a downward gradient toward the drainage hole 89 is formed in the bottom wall 75 of the sheath introduced portion 37. In the housing 35, the sheath introduced portion 37 has a substantially quadrangular pyramid shape. In the sheath introduced portion 37, this one side surface having a substantially quadrangular pyramid shape becomes the bottom wall 75. That is, one side surface having a substantially quadrangular pyramid shape becomes the tilted plate 93. The drainage hole 89 is formed on a tilted lower end side of the tilted plate 93 in a slit shape along the liquid intrusion prevention wall 77.

In the housing 35, the sponges 87 are sandwiched by the upper housing 47 and the lower housing 49. In the example of this configuration, the sponges 87 are constituted of a pair of upper and lower sponges. A pair of sponges 87 forms a hexahedron. Inside the housing 35, at least a part of the wires (the transmission cable 29 and the light fibers 31) in the extending direction between the base end aperture portion 55 and the liquid intrusion prevention wall 77 is interposed between the pair of sponges 87 above the tilted plate 93.

Inside the housing, as in the illustrated example, the sponges 87 can be at positions where sponge rear end surfaces 95 come into contact with the liquid intrusion prevention wall 77 standing from the edge of the drainage hole 89. In addition, the sponge rear end surfaces 95 of the sponges 87 may be positioned on the front side such that a gap is formed between the sponges 87 and the liquid intrusion prevention wall 77.

The sponges described above are merely an example, and a raw material, for example, resin or gel blocking or absorbing moisture may be used.

In the liquid intrusion prevention wall 77, a foreign substance insertion prevention wall 97 extending along the bottom wall 75 (including a case not parallel to the bottom wall 75) above the drainage hole 89 is formed on a surface on a side opposite to the substrate accommodation portion 59. The foreign substance insertion prevention wall 97 is not necessarily parallel to the tilted plate 93. In the example of this configuration, the foreign substance insertion prevention wall 97 extends in the horizontal direction. At least a part of the lower surfaces of the sponges 87 is placed in the foreign substance insertion prevention wall 97. The foreign substance insertion prevention wall 97 may be formed to have a tilted gradient toward the front. Accordingly, the liquid 67 on the upper surface of the foreign substance insertion prevention wall 97 can be more likely to fall down.

Next, an operation of the configuration described above will be described.

Figure 7:
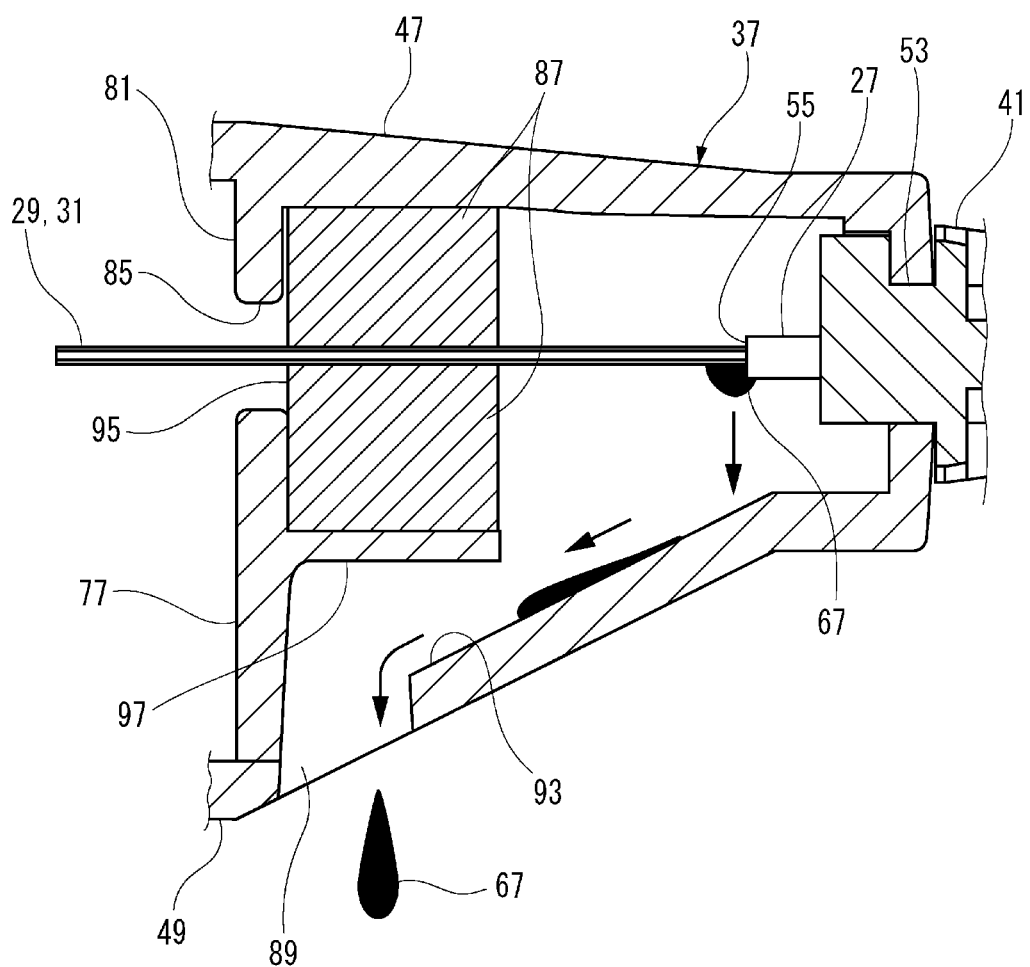
FIG. 7 is a view describing an operation illustrating a flow path of liquid falling down from a base end aperture portion.

FIG. 7 is a view describing an operation illustrating a flow path of the liquid 67 falling down from the base end aperture portion 55.

In the plug 100 for endoscope of Embodiment 1, it is not possible to completely deny a possibility that the sheath 27 having a small diameter (outer diameter of approximately 2 mm or smaller) is damaged due to contact or the like with a foreign substance and the liquid 67 intrudes into the sheath, when the inserted tip portion 19 and the sheath 27 are inserted into a blood vessel of a patient. For example, in regard to the liquid 67 that has intruded into the sheath, if the amount of intrusion is significant, the liquid 67 flows into the housing from the base end aperture portion 55 of the sheath 27 along the wires due to a capillary phenomenon. At this time, in the plug 100 for endoscope in the example of this configuration, as illustrated in FIG. 7, most of the liquid 67 that has flowed in from the base end aperture portion 55 falls down due to gravity from the base end aperture portion or the wires in the vicinity of the base end aperture portion. The fallen liquid 67 adheres to the bottom wall 75 of the housing 35. In the plug 100 for endoscope, if the liquid 67 that has adhered to the bottom wall 75 tends to intrude into the substrate accommodation portion 59 along the bottom wall 75, the liquid intrusion prevention wall 77 stops the liquid 67. That is, the liquid intrusion prevention wall 77 partitions (isolates) the substrate accommodation portion 59 from the bottom wall 75 in which the drainage hole 89 is provided. Accordingly, the liquid 67 that has flowed in from the base end aperture portion 55 of the sheath 27 can be less likely to adhere to the substrate 61.

If the amount of falling liquid increases, the liquid 67 falls through the drainage hole 89 formed in the bottom wall 75 and is drained out of the housing 35. Accordingly, it is possible to minimize an electric shock to a patient caused by liquid flowing in from the sheath 27 and adhering to the substrate 61, and short circuit of the substrate 61.

In addition, in the plug 100 for endoscope, if the liquid 67 that has adhered to the bottom wall 75 reaches the amount to flow along the bottom wall 75, the liquid 67 flows down along the downward gradient of the tilted plate 93. The liquid 67 that has flowed along the tilted plate 93 reaches the drainage hole 89 disposed in a downward direction of the tilted plate 93 and is drained out of the housing 35 through the drainage hole 89. Accordingly, the liquid 67 is not accumulated in the bottom wall 75, and after the liquid 67 adheres to the bottom wall 75, the liquid 67 is promptly drained out of the housing 35.

Figure 8:
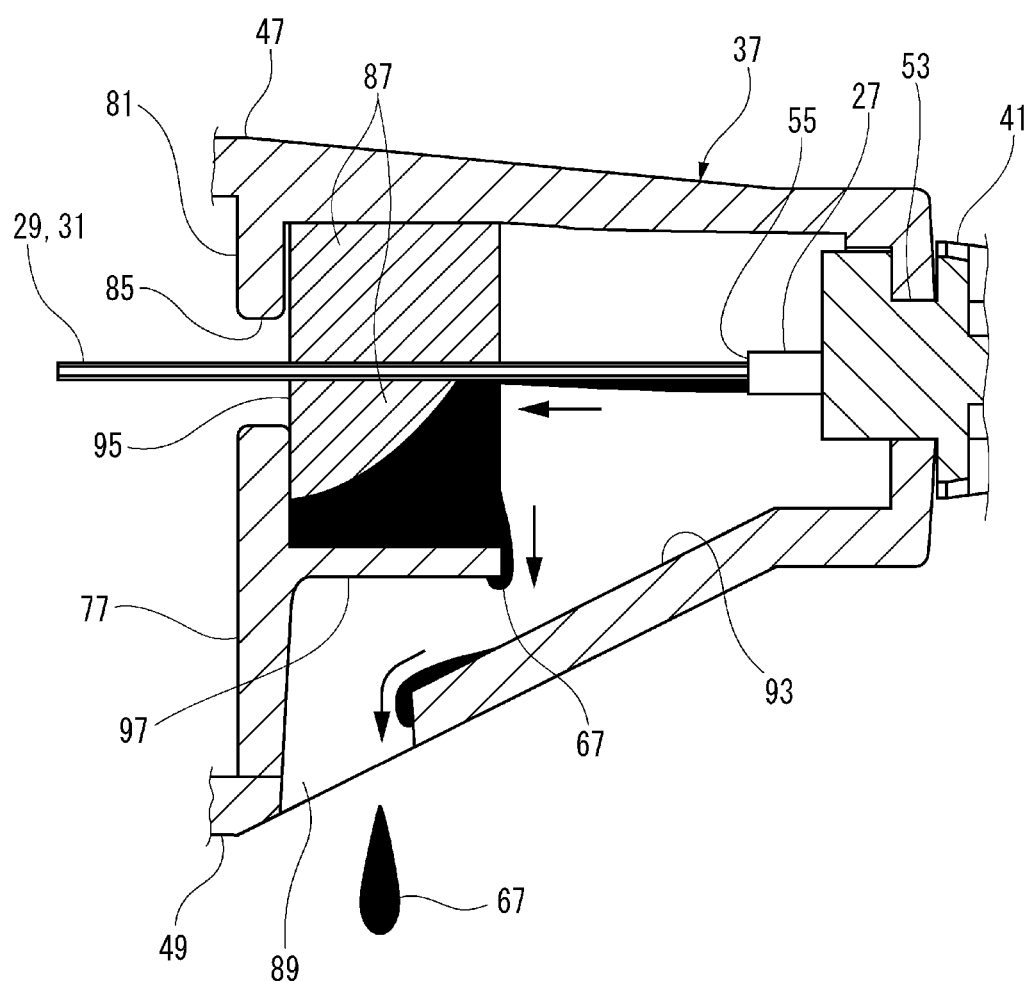
FIG. 8 is a view describing an operation illustrating a flow path of liquid adsorbed into sponges.

FIG. 8 is a view describing an operation illustrating a flow path of the liquid 67 adsorbed into the sponges 87.

In addition, in the plug 100 for endoscope, as illustrated in FIG. 8, it is assumed that the liquid 67, which has flowed in from the base end aperture portion 55 and has not fallen down from the base end aperture portion or the wires in the vicinity of the base end aperture portion, flows along the wires. Between the base end aperture portion 55 and the liquid intrusion prevention wall 77, the liquid 67 flowing along the wires is temporarily absorbed by the sponges 87 having the wires interposed therebetween. If the liquid 67 that has been absorbed by the sponges 87 reaches a predetermined amount, the liquid 67 falls due to gravity. Similar to that described above, after adhering to the bottom wall 75, the fallen liquid 67 flows and falls through the drainage hole 89 and is drained out of the housing 35. Accordingly, since the liquid 67 flowing along the wires can also be adsorbed by the sponges 87, the liquid 67 does not intrude into the substrate accommodation portion 59, so that an electric shock can be more reliably prevented.

In the plug 100 for endoscope, it is assumed that the base end aperture portion 55 of the sheath 27 is filled with an adhesive and is sealed, and a gap between the sheath 27 and the wires is blocked by this sealing portion. In this case, the wires are integrally fixed to the sheath 27 by the sealing portion. Incidentally the sheath 27 has to be freely bent when inserted into a blood vessel of a patient. However, if the wires that have already been connected and fixed to the inserted tip portion 19 are also fixed to the base end aperture portion 55, both ends in the extending direction are integrally fixed. If the sheath 27 is bent in this state, the wires in a bundle shape tend to swell inside the sheath due to the difference in the radius of curvature.

In this case, if the swelling is restricted by an inner circumferential wall of the sheath 27, a possibility of damage to the light fibers 31 having a particularly small diameter increases.

Therefore, the plug 100 for endoscope in the example of this configuration has a structure is not provided with a sealing portion which integrally fixes the wires to the base end aperture portion 55 of the sheath 27. Then, the liquid 67 flowing along the wires from the base end aperture portion 55 is adsorbed by the sponges 87. The liquid 67 intruding into the substrate accommodation portion 59 is reliably minimized by using the sponges 87 while avoiding integral fixing of the wires and allowing the wires to be relatively slidable.

In addition, in the plug 100 for endoscope, if a foreign substance (an injection needle, tweezers, or the like) is inserted into the drainage hole 89 from the outside of the housing 35, this foreign substance hits the foreign substance insertion prevention wall 97. Accordingly, damage to the wires caused by a foreign substance inserted through the drainage hole 89 is minimized.

In addition, in the plug 100 for endoscope, even in case where a significant drainage hole 89 is formed, deterioration in strength of the housing 35 can be minimized by partitioning the drainage hole 89 using the rib 91. Particularly, in order to realize favorable drainage of the liquid 67, it is preferable that the drainage hole 89 is formed in a slit shape elongated along the liquid intrusion prevention wall 77. In this case, in the housing 35, deterioration in strength can be minimized by providing the rib 91 at a position bisecting the drainage hole 89 in the longitudinal direction of the drainage hole 89. In addition, the rib 91 is disposed immediately below the wires. Accordingly, together with the foreign substance insertion prevention wall 97 described above, the rib 91 can further prevent a foreign substance from coming into contact with the wires.

Then, in the plug 100 for endoscope, one side surface of the substantially quadrangular pyramid shape becomes the bottom wall 75 of the housing 35. Therefore, the bottom wall 75 of the sheath introduced portion 37 has a triangular shape. The triangular bottom wall 75 becomes the tilted plate 93 having a downward gradient from the apex portion to the bottom side. In the tilted triangular bottom wall 75, the drainage hole 89 having a slit shape elongated along the bottom side can be formed on the side of the bottom side. That is, it is possible to easily form the slit-shaped drainage hole 89 with favorable drainage by having the substantially quadrangular pyramid-shaped sheath introduced portion 37.

Moreover, in the plug 100 for endoscope, the sheath introduced portion 37 is formed in a substantially quadrangular pyramid shape, and the liquid intrusion prevention wall 77 stands at a position forming a bottom surface of the substantially quadrangular pyramid shape. A side opposite to the sheath introduced portion 37 with the liquid intrusion prevention wall 77 interposed therebetween becomes the quadrangular cylinder-shaped housing main body 39. Accordingly, in the housing 35, it is possible to form the sheath introduced portion 37 having the tilted plate 93 to which a function of draining the liquid 67 is applied, and the housing main body 39 in which large volume for accommodating the substrate 61 is ensured, in efficiently compact shapes.

Therefore, according to the plug 100 for endoscope of Embodiment 1, an electric shock to a patient can be minimized when liquid intrudes into a sheath.

Embodiment 2

Next, a plug for endoscope according to Embodiment 2 will be described. In Embodiment 2, the same reference signs are applied to the same members as the members illustrated in Embodiment 1, and duplicated description will be omitted.

Figure 9:
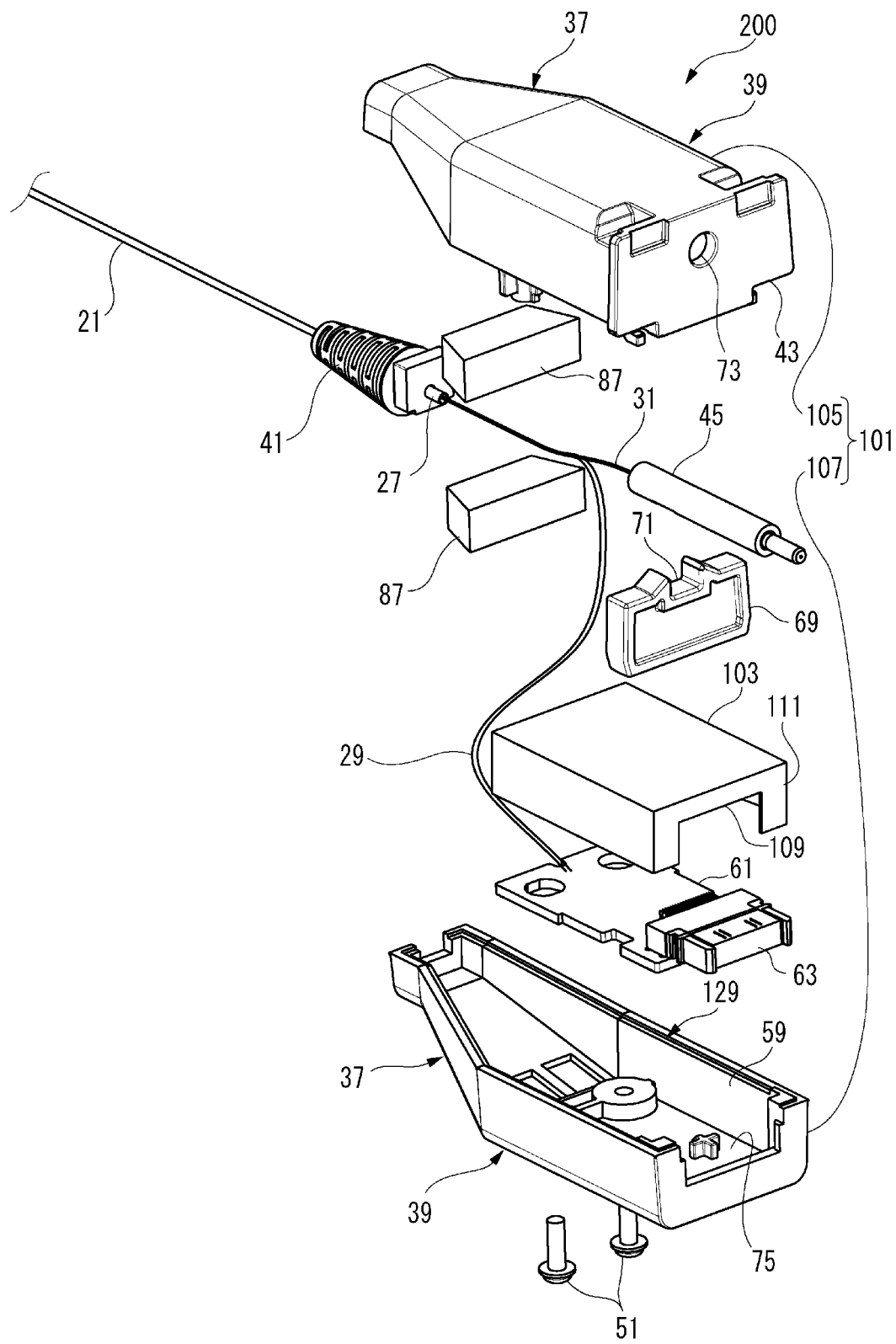
FIG. 9 is an exploded perspective view of a plug for endoscope of Embodiment 2.

FIG. 9 is an exploded perspective view of a plug 200 for endoscope of Embodiment 2.

The plug 200 for endoscope according to Embodiment 2 includes a cover 103 which is water-tightly penetrated by a part of the plurality of wires (the transmission cable 29) provided inside a housing 101 and water-tightly covers the substrate 61. The housing 101 is constituted of an upper housing 105 and a lower housing 107 in which the liquid intrusion prevention wall 77 described above is not formed. In the configuration of FIG. 9, although the liquid intrusion prevention wall 77 is not formed, forming the liquid intrusion prevention wall 77 is not excluded in Embodiment 2.

The cover 103 is formed in a substantially rectangular flat parallelepiped box shape of which a lower surface is open. It is desirable that the cover 103 has insulating properties. For example, the cover 103 is integrally molded by using a synthetic resin material. The cover 103 can cover the substrate 61 by accommodating the substrate 61 from the aperture on the lower surface. The cover 103 has a terminal derivation portion 109 in a rear wall portion 111 penetrated by the card edge terminal 63.

Figure 10:
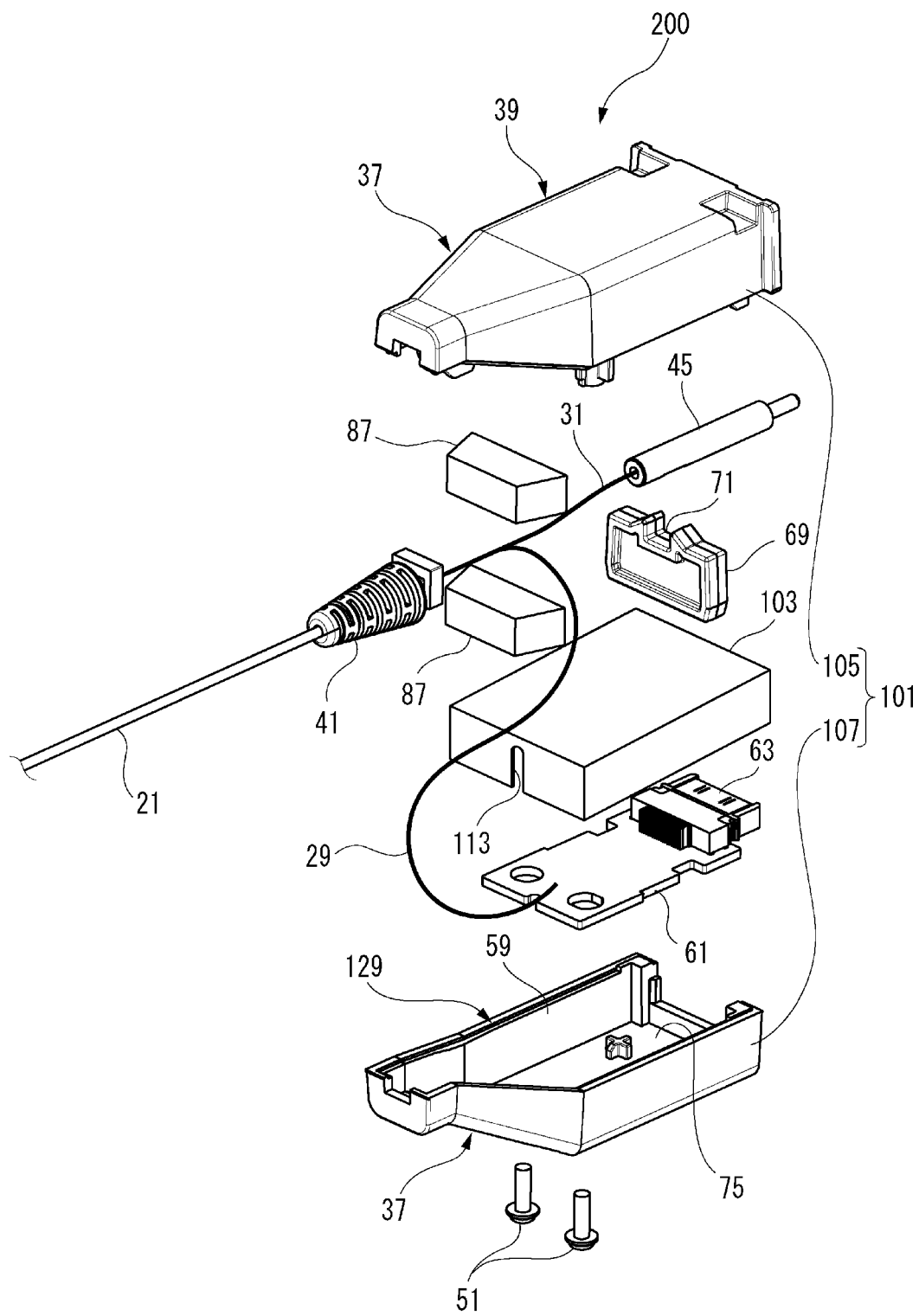
FIG. 10 is a perspective view of that in FIG. 9 seen from a front side obliquely above a sheath introduced portion.

FIG. 10 is a perspective view of that in FIG. 9 seen from a front side obliquely above the sheath introduced portion 37.

In the other side wall of the cover 103, a U-shaped groove 113 is cut into the aperture portion side. The transmission cable 29 can be inserted through the U-shaped groove 113. The light fibers 31 having no risk of an electric shock is connected to the ferrule 45 without being covered with the cover 103.

Figure 11:
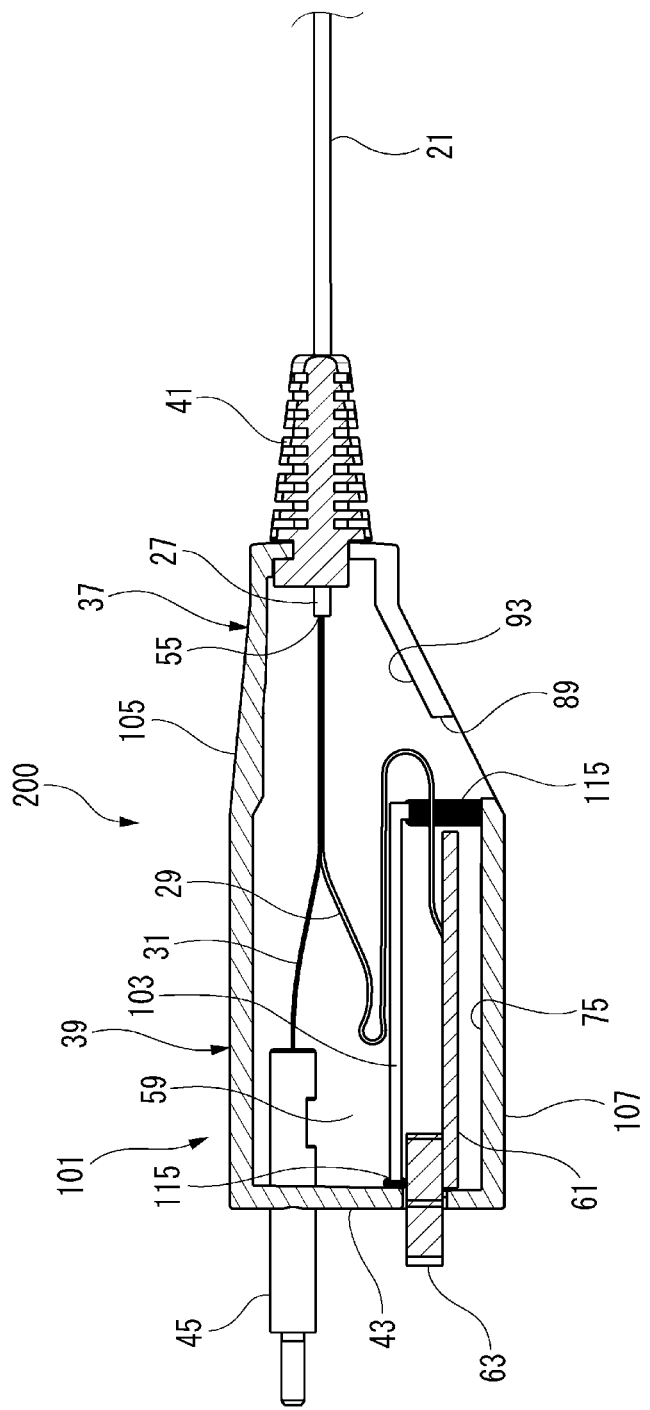
FIG. 11 is a longitudinal cross-sectional view of the plug for endoscope of Embodiment 2.

FIG. 11 is a longitudinal cross-sectional view of the plug 200 for endoscope of Embodiment 2.

In the cover 103 covering the substrate 61, the aperture portion is water-tightly sealed with respect to the bottom wall 75 by an adhesive 115. In addition, in the cover 103, a part between the card edge terminal 63 and the terminal derivation portion 109 and a part between the conductive transmission cable 29 and the U-shaped groove 113 are water-tightly sealed by the adhesive 115. Accordingly, even if the transmission cable 29 is conductive, since a part between the transmission cable 29 and the U-shaped groove 113 is water-tightly sealed by the adhesive 115, the liquid 67 adhering to the substrate 61 is minimized, and there is no risk of an electric shock. In the cover 103, all of the gaps are blocked by the adhesive 115, so that the substrate 61 is water-tightly sealed. Therefore, the same member as the plug 100 for endoscope can be used as the plug 200 for endoscope, excluding the housing 101 and the cover 103 different from those in Embodiment 1.

In the plug 200 for endoscope according to Embodiment 2, the liquid 67 adhering to the substrate 61 can be minimized by water-tightly sealing only the substrate 61 having a risk of an electric shock. As a result, it is possible to minimize an electric shock to a patient caused by short circuit of the substrate 61. In addition, according to the plug 200 for endoscope, the housing 101 can be simplified by omitting the liquid intrusion prevention wall 77.

Embodiment 3

Next, a plug for endoscope according to Embodiment 3 will be described. In Embodiment 3, the same reference signs are applied to the same members as the members illustrated in Embodiment 1, and duplicated description will be omitted.

Figure 12:
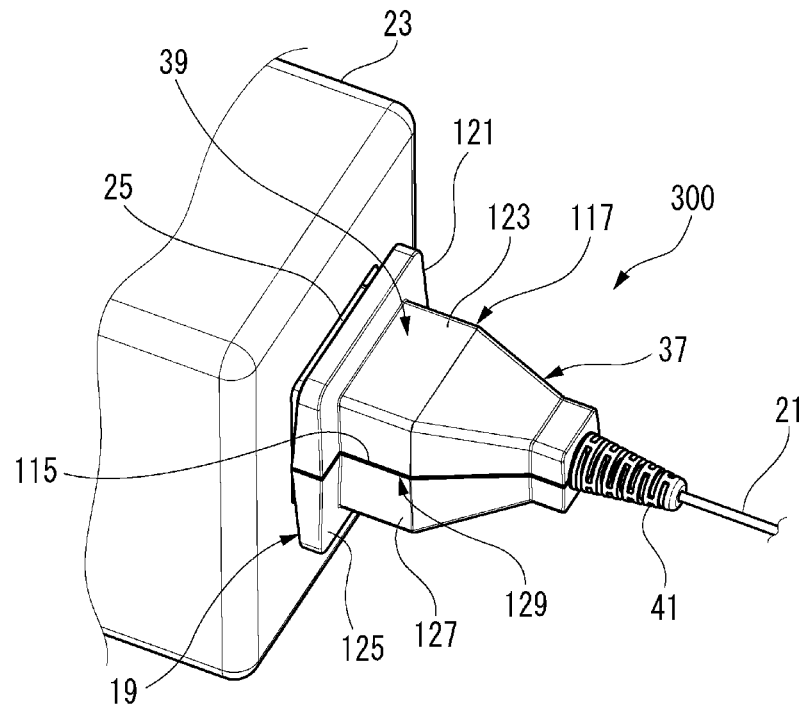
FIG. 12 is a perspective view illustrating a plug for endoscope of Embodiment 3 together with a part of a relay unit.

FIG. 12 is a perspective view illustrating a plug 300 for endoscope of Embodiment 3 together with a part of the relay unit 23.

In the plug 300 for endoscope according to Embodiment 3, in an outer circumference of a housing 117, a flange portion 119 bulging out from the outer circumference is entirely formed over the outer circumference. The housing 117 is constituted of an upper housing 123 in which an upper flange portion 121 is formed, and a lower housing 127 in which a lower flange portion 125 is formed. In the housing 117, since the upper housing 123 and the lower housing 127 are combined, the flange portion 119 bulges out entirely over the outer circumference.

Figure 13:
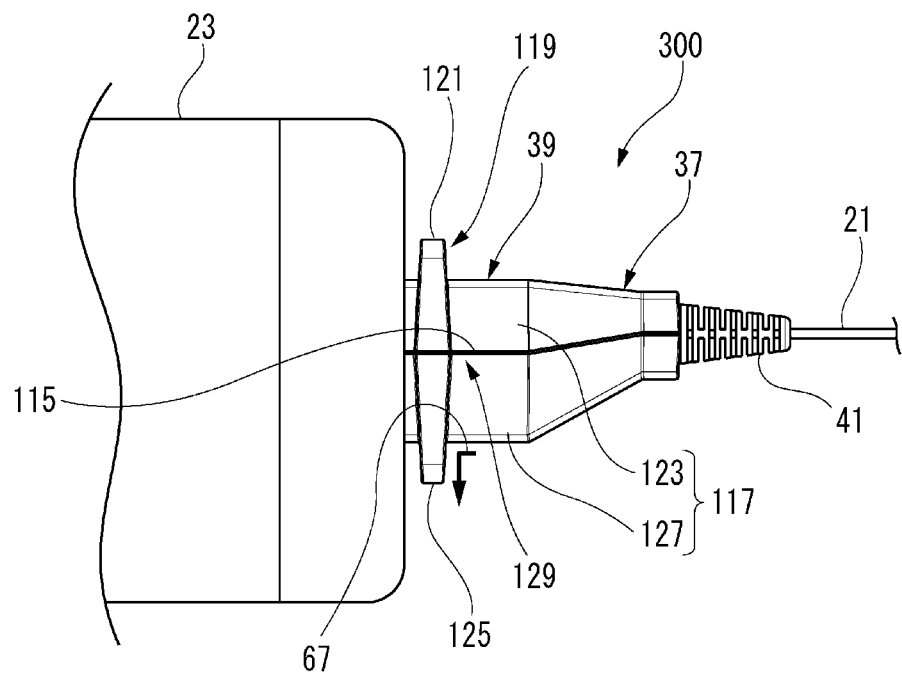
FIG. 13 is a side view of that in FIG. 12.

FIG. 13 is a side view of that in FIG. 12.

In the plug 300 for endoscope connected to the socket portion 25 of the relay unit 23, the lower flange portion 125 is disposed to be hung between the lower surface of the lower housing 127 and the socket portion 25. Therefore, for example, even if the liquid 67 flows along the lower surface of the lower housing 127 through the drainage hole 89, the lower flange portion 125 stops the liquid 67, so that the liquid 67 falls down from a lower end of the lower flange portion 125. Therefore, infiltration of the liquid 67 flowing along the lower surface of the lower housing 127 into the socket portion 25 can be minimized. Therefore, the same member as the plug 100 for endoscope can be used as the plug 300 for endoscope, excluding the housing 117 different from that in Embodiment 1.

Figure 14:
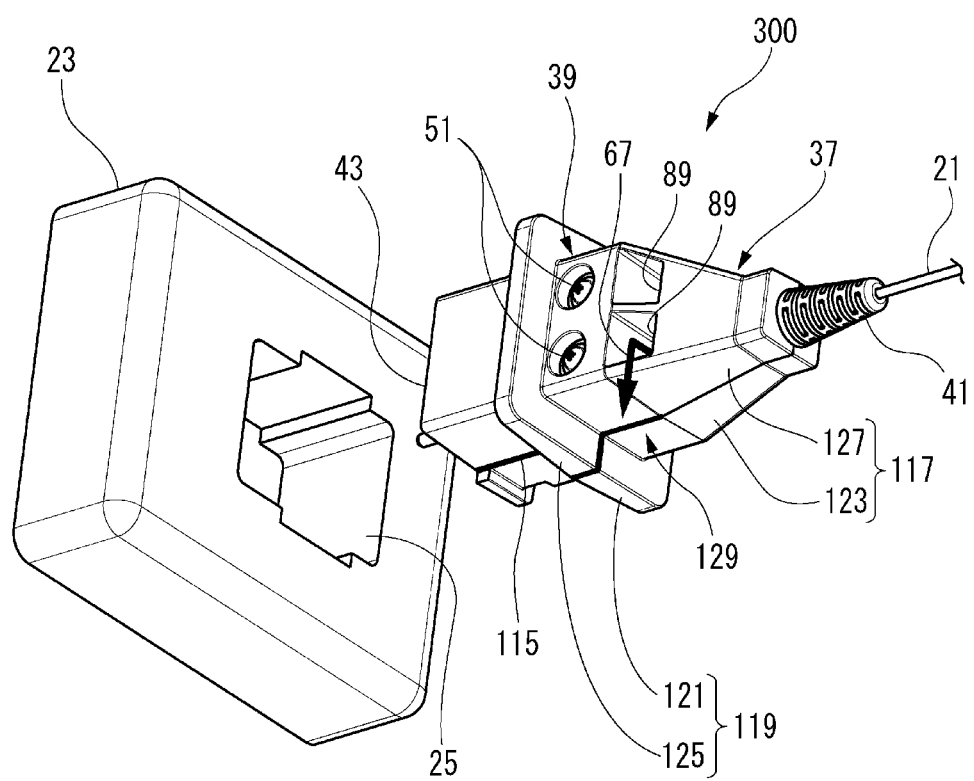
FIG. 14 is an exploded perspective view of a state where the plug for endoscope and the relay unit in FIG. 13 are rotated 90° about a soft portion.

FIG. 14 is an exploded perspective view of a state where the plug 300 for endoscope and the relay unit 23 in FIG. 13 are rotated 90° about the soft portion 21.

In addition, in the plug 300 for endoscope according to Embodiment 3, since the flange portion 119 is entirely formed over the circumference, even in a case where the plug 300 for endoscope is laid down together with the relay unit 23, infiltration of the liquid 67 into the socket portion 25 can be minimized.

Moreover, since the flange portion 119 is provided, when a practitioner connects the plug 300 for endoscope to the relay unit 23, the practitioner grips a hand side from the flange portion 119, so that it is possible to prevent the practitioner from coming into contact with an area on the relay unit 23 side which is not sterilized, and it is possible to prevent sterilized gloves of the practitioner and an operating field from being contaminated.

Embodiment 4

Next, a plug for endoscope according to Embodiment 4 will be described. In Embodiment 4, the same reference signs are applied to the same members as the members illustrated in Embodiment 1, and duplicated description will be omitted.

Figure 15:
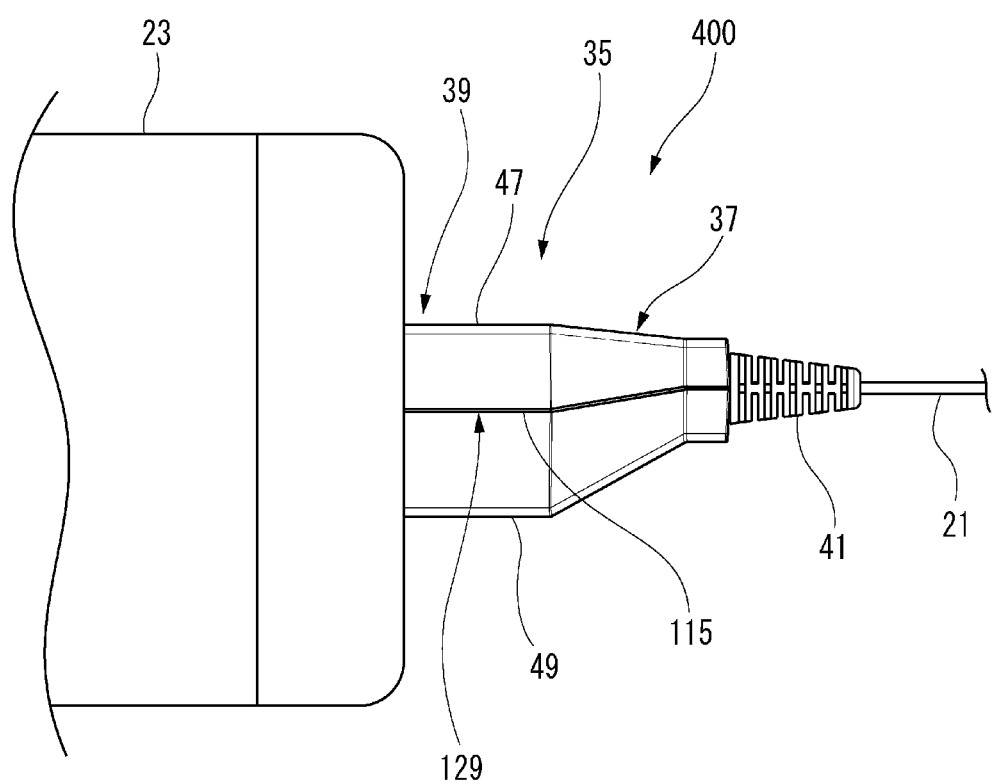
FIG. 15 is a side view illustrating a plug for endoscope of Embodiment 4 together with a part of the relay unit.

FIG. 15 is a side view illustrating a plug 400 for endoscope of Embodiment 4 together with a part of the relay unit 23.

In the plug 400 for endoscope according to Embodiment 4, similar to the plug 100 for endoscope, the housing 35 is configured to be bisected into the upper housing 47 and the lower housing 49 with an axis line of the substantially quadrangular pyramid shape as a boundary. A bonding portion 129 between the upper housing 47 and the lower housing 49 is water-tightly sealed by the adhesive 115, so that they are integrally assembled. Therefore, the same member as the plug 100 for endoscope can be used as the plug 400 for endoscope, excluding the bonding portion 129 which is water-tightly sealed by the adhesive 115, thereby being different from that in Embodiment 1.

Figure 16:
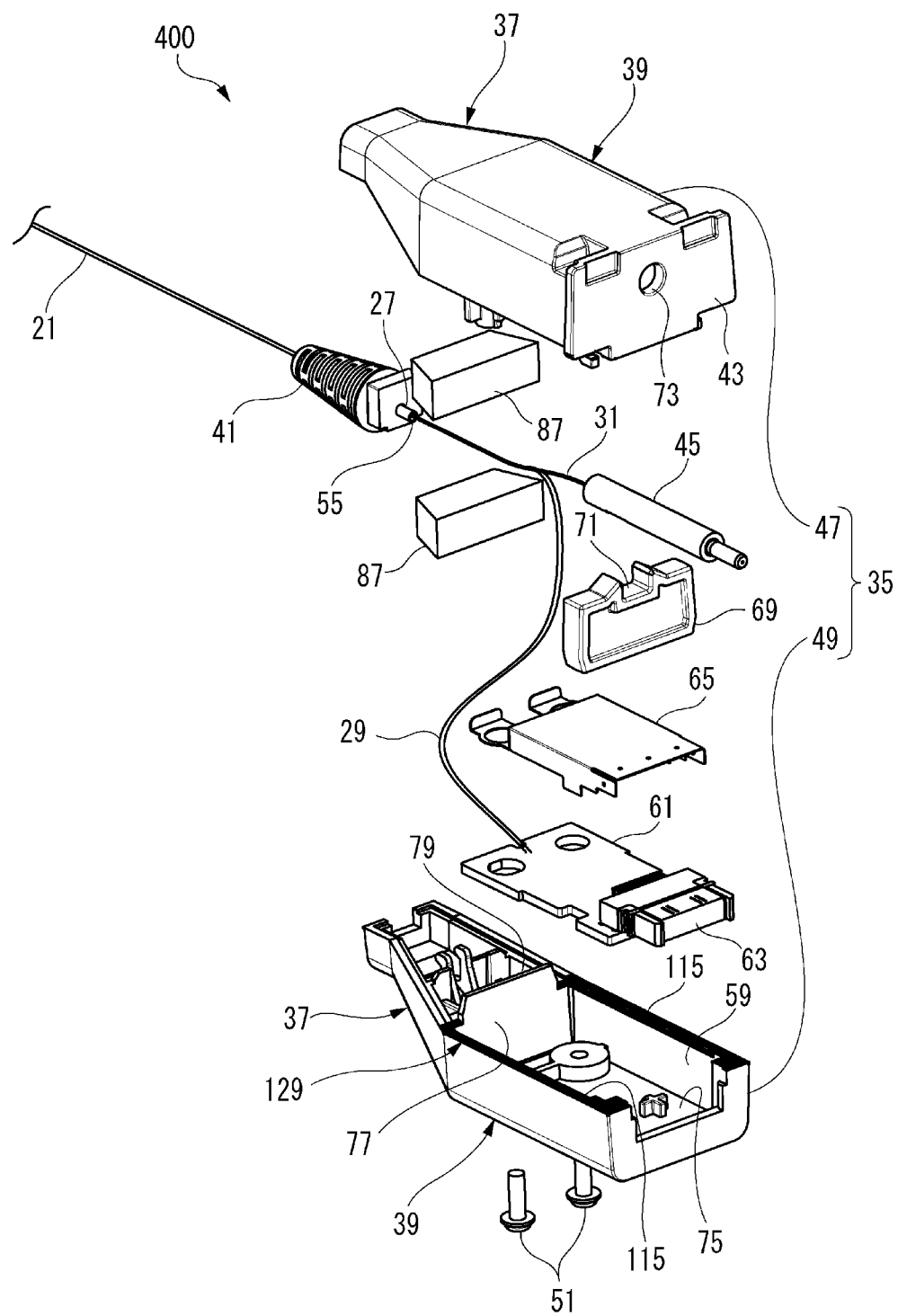
FIG. 16 is an exploded perspective view of the plug for endoscope of Embodiment 4.

FIG. 16 is an exploded perspective view of the plug 400 for endoscope of Embodiment 4.

In the plug 400 for endoscope according to Embodiment 4, since the bonding portion 129 between the upper housing 47 and the lower housing 49 is water-tightly sealed by the adhesive 115, infiltration of the liquid 67 flowing along the outside of the housing 35 into the housing 35 or the socket portion 25 of the relay unit 23 can be minimized.

The water-tight structure of the bonding portion 129 using the adhesive 115 can also be applied to the plug 100 for endoscope, the plug 200 for endoscope, and the plug 300 for endoscope described above. Particularly, in the plug 300 for endoscope, the stopping effect at the time of being laid down as illustrated in FIG. 14 can be more reliably realized by water-tightly sealing the bonding portion 129 between the upper flange portion 121 and the lower flange portion 125 using the adhesive 115.

Hereinabove, the embodiments have been described with reference to the drawings. However, there is no need to mention that the present disclosure is not limited to the examples. It is clearly understood that those skilled in the art can conceive various modification examples or revision examples within the scope disclosed in the aspects of the present disclosure and those naturally belong to the technical scope of the present disclosure. In addition, within a range not departing from the gist of the invention, each of the constituent elements in the embodiments described above can be combined in any desired manner.

For example, the embodiments described above have a configuration including an image capturing element at an inserted tip portion. However, the plugs for endoscope may be applied to a fiber endoscope including no image capturing element.

In addition, in the embodiments described above, an example of a case where liquid flowing into a housing from a sheath is body fluid, for example, blood has been described. However, liquid may be a different kind of body fluid for example, gastric juice, bile, or pancreatic juice.

The present disclosure is useful as a plug for endoscope, in which an electric shock to a patient can be minimized when a sheath is damaged while liquid intrudes into the sheath during a surgical operation, for example.

The present application is based upon Japanese Patent Application (Patent Application No. 2017-177949) filed on Sep. 15, 2017, the contents of which are incorporated herein by reference.

What is claimed is:

1. A plug for endoscope comprising:
a flexible tube-shaped sheath through which a plurality of wires are inserted, the plurality of wires being connected to an insertion tip portion having an image capturing portion; and
a housing having a substrate accommodation portion and a sheath introduced portion,
wherein the substrate accommodation portion accommodates a substrate, a base end aperture portion of the sheath passed through an opening of the housing is arranged in the sheath introduced portion, and a part of the plurality of wires derived from the base end aperture portion is connected to the substrate,
wherein a liquid intrusion prevention wall is provided to stand on a bottom wall of the housing without touching a top wall of the housing to allow a portion of the plurality of wires to pass over the liquid intrusion prevention wall, and the bottom wall is arranged under side of the base end aperture portion of the sheath in a substantially vertical direction, and the substrate accommodation portion and the sheath introduced portion are spatially isolated from each other, and
wherein a plurality of liquid absorption pads are in contact with one another and disposed adjacent to the liquid intrusion prevention wall, and at least a part of the plurality of wires is interposed between the plurality of liquid absorption pads to allow the plurality of wires to extend into the substrate accommodation portion from the sheath introduced portion while impeding liquid from entering into the substrate accommodation portion.

2. The plug for endoscope according to claim 1,
wherein the plurality of wires are not fixed inside the sheath and to the base end aperture portion so as not to hinder relative sliding properties of the plurality of wires inside the sheath, at the base end aperture portion, and inside the housing when the sheath is bent.

3. The plug for endoscope according to claim 1,
wherein the plurality of wires are slidingly movable with respect to the sheath and the base end aperture portion; and
wherein when the sheath is bent, the plurality of wires move with respect to the sheath, the base end aperture portion and the housing.

4. The plug for endoscope according to claim 1,
wherein a part or all of the plurality of wires are disposed with slack inside the sheath or inside the plug for endoscope so that when the sheath is bent, the plurality of wires are movable with respect to the sheath, the base end aperture portion and the housing.

5. The plug for endoscope according to claim 1,
wherein the plurality of wires include a glass fiber and a conductive transmission cable.

6. The plug for endoscope according to claim 1, further comprising:
a cover that is provided inside the housing, and water-tightly covers the substrate,
wherein a part of the plurality of wires which water-tightly penetrates the cover includes a conductive transmission cable.

7. The plug for endoscope according to claim 1,
wherein a drainage hole is opened in the bottom wall of the housing and drains liquid that has intruded from the base end aperture portion out of the housing.

8. The plug for endoscope according to claim 7,
wherein a tilted face that has a downward gradient toward the drainage hole is formed on the bottom wall.

9. The plug for endoscope according to claim 8,
wherein the plurality of liquid absorption pads includes one or more sponges.

10. The plug for endoscope according to claim 8,
wherein a drainage hole is opened in the bottom wall of the housing and drains liquid that has intruded from the base end aperture portion out of the housing; and
wherein a foreign substance insertion prevention wall that extends along the bottom wall above the drainage hole is provided on a surface of the liquid intrusion prevention wall on a side opposite to the substrate accommodation portion to support at least a part of the plurality of liquid absorption pads.

11. The plug for endoscope according to claim 7,
wherein a rib that extends below the wires in a direction along the wires and connects a pair of facing positions to each other on an inner circumference of the drainage hole in the extending direction, is provided in the drainage hole.

12. The plug for endoscope according to claim 1,
wherein the sheath introduced portion is formed in a substantially quadrangular pyramid-shape and is formed on a side where the sheath is fixed; and
wherein the sheath introduced portion is arranged so that an axis line which is perpendicular to a substantially quadrangular pyramid-shaped bottom surface of the sheath introduced portion and passes through an apex portion of the sheath introduced portion is disposed in a direction along an extending direction of the wires.

13. The plug for endoscope according to claim 12,
wherein the housing is formed by connecting a quadrangular cylinder-shaped housing main body to the substantially quadrangular pyramid-shaped bottom surface side of the sheath introduced portion.

14. The plug for endoscope according to claim 1,
wherein a flange portion bulges out from an outer circumference of the housing and is entirely formed over the outer circumference.

15. The plug for endoscope according to claim 1,
wherein the housing is configured to be bisected into an upper housing and a lower housing with an axis line of a substantially quadrangular pyramid shape as a boundary, and a bonding portion of the upper housing and the lower housing is water-tightly sealed by an adhesive such that the upper housing and the lower housing are integrally assembled.

16. The plug for endoscope according to claim 1,
wherein a top edge of the liquid intrusion prevention wall is entirely linear from one end to an opposing end.

17. The plug for endoscope according to claim 1,
wherein the plurality of liquid absorption pads are disposed to contact the top wall of the housing but not the bottom wall of the housing.

18. A plug for endoscope comprising:
a flexible tube-shaped sheath through which a plurality of wires are inserted, the plurality of wires being connected to an insertion tip portion having an image capturing portion; and
a housing having a sheath introduced portion disposed in a base end side of the sheath and a substrate accommodation portion which accommodates a substrate,
wherein a liquid intrusion prevention wall is provided to stand on a bottom wall of the housing without touching a top wall of the housing to allow a portion of the plurality of wires to pass over the liquid intrusion prevention wall, the bottom wall is arranged under side of a base end of the sheath in a substantially vertical direction, and the substrate accommodation portion and the sheath introduced portion are spatially isolated from each other, wherein a part of the plurality of wires derived from the base end of the sheath is connected to the substrate, and the plurality of wires are disposed with slack and are not fixed in the housing, and wherein a plurality of liquid absorption pads are in contact with one another and disposed adjacent to the liquid intrusion prevention wall, and at least a part of the plurality of wires is interposed between the plurality of liquid absorption pads to allow the plurality of wires to extend into the substrate accommodation portion from the sheath introduced portion while impeding liquid from entering into the substrate accommodation portion.

19. A plug for endoscope comprising:

a flexible tube-shaped sheath through which a plurality of wires are inserted, the plurality of wires being connected to an insertion tip portion having an image capturing portion; and a housing having a sheath introduced portion disposed in a base end side of the sheath and a substrate accommodation portion which accommodates a substrate, wherein the substrate accommodation portion is covered with a water-tight structure, and the substrate accommodation portion and the sheath introduced portion are spatially isolated from each other, wherein a part of the plurality of wires derived from a base end of the sheath is connected to the substrate, and the plurality of wires are disposed with slack and are not fixed in the housing, wherein the substrate accommodation portion and the sheath introduced portion are spatially isolated from each other via at least a plurality of liquid absorption pads that are in contact with one another, and wherein at least a part of the plurality of wires is interposed between the plurality of liquid absorption pads to allow the plurality of wires to extend into the substrate accommodation portion from the sheath introduced portion while impeding liquid from entering into the substrate accommodation portion.

20. A plug for endoscope comprising:

a flexible tube-shaped sheath through which a plurality of wires are inserted, the plurality of wires being connected to an insertion tip portion having an image capturing portion; and a housing having a substrate accommodation portion and a sheath introduced portion, wherein the substrate accommodation portion accommodates a substrate, a base end aperture portion of the sheath passed through an opening of the housing is arranged in the sheath introduced portion, and a part of the plurality of wires derived from the base end aperture portion is connected to the substrate, wherein a liquid intrusion prevention wall is provided to stand on a bottom wall of the housing without touching a top wall of the housing to allow a portion of the plurality of wires to pass over the liquid intrusion prevention wall, and the bottom wall is arranged under side of the base end aperture portion of the sheath in a substantially vertical direction, and the substrate accommodation portion and the sheath introduced portion are spatially isolated from each other, and wherein a plurality of liquid absorption pads that are in contact with one another is disposed adjacent to the liquid intrusion prevention wall, and a part of the plurality of wires is inserted through the plurality of liquid absorption pads to allow the wires to extend into the substrate accommodation portion from the sheath introduced portion while impeding liquid from entering into the substrate accommodation portion.

* * * * *